(12) United States Patent
Sobel et al.

(10) Patent No.: US 11,285,092 B2
(45) Date of Patent: Mar. 29, 2022

(54) COSMETIC BASE COMPOSITIONS AND ASSOCIATED COSMETIC COMPOSITIONS

(71) Applicant: Sobel Brands, LLC, New York, NY (US)

(72) Inventors: Howard Sobel, New York, NY (US); John Kressaty, Brentwood, TN (US)

(73) Assignee: Sobel Brands, LLC, New York, NY (US)

( * ) Notice: Subject to any disclaimer, the term of this patent is extended or adjusted under 35 U.S.C. 154(b) by 0 days.

(21) Appl. No.: 16/535,964

(22) Filed: Aug. 8, 2019

(65) Prior Publication Data

US 2020/0046622 A1 Feb. 13, 2020

Related U.S. Application Data

(60) Provisional application No. 62/715,951, filed on Aug. 8, 2018.

(51) Int. Cl.

| | |
|---|---|
| *A61K 8/55* | (2006.01) |
| *A61K 8/67* | (2006.01) |
| *A61K 8/34* | (2006.01) |
| *A61K 8/27* | (2006.01) |
| *A61K 8/29* | (2006.01) |
| *A61K 8/36* | (2006.01) |
| *A61K 8/81* | (2006.01) |
| *A61K 8/92* | (2006.01) |
| *A61K 8/04* | (2006.01) |

(52) U.S. Cl.
CPC ............... *A61K 8/553* (2013.01); *A61K 8/27* (2013.01); *A61K 8/29* (2013.01); *A61K 8/342* (2013.01); *A61K 8/345* (2013.01); *A61K 8/361* (2013.01); *A61K 8/671* (2013.01); *A61K 8/676* (2013.01); *A61K 8/678* (2013.01); *A61K 8/8147* (2013.01); *A61K 8/92* (2013.01); *A61K 8/042* (2013.01)

(58) Field of Classification Search
None
See application file for complete search history.

(56) References Cited

U.S. PATENT DOCUMENTS

| | | | |
|---|---|---|---|
| 7,001,604 B2 | 2/2006 | Albrecht et al. | |
| 7,968,129 B2 * | 6/2011 | Golz-Berner | A61K 8/671 424/725 |
| 9,974,745 B2 | 5/2018 | Mannino et al. | |
| 2005/0079210 A1 | 4/2005 | Gupta | |
| 2005/0124705 A1 * | 6/2005 | Schreiber | A61Q 5/00 516/53 |
| 2011/0027327 A1 * | 2/2011 | Albrecht | A61K 8/9761 424/401 |
| 2015/0196482 A1 * | 7/2015 | Bleyer | A61K 31/355 424/59 |
| 2015/0359723 A1 * | 12/2015 | Kim | A61K 8/68 424/401 |

FOREIGN PATENT DOCUMENTS

| | | |
|---|---|---|
| WO | 2015024055 A1 | 2/2015 |
| WO | 2017063748 A1 | 4/2017 |
| WO | 2018069814 A1 | 4/2018 |

OTHER PUBLICATIONS

The Olive Oil Source. "Omega-3 and Omega-6 fatty acids." The Olive Oil Source, 2013, www.oliveoilsource.com/definition/omega-3-and-omega-6-fatty-acids (Year: 2013).*
Andrea, 70 Non-Comedogenic Facial Oils For Clear Skin, Oct. 2, 2015, The Best Organic Skin Care (Year: 2015).*
Shea Butter RBD Product Data Sheet, Jul. 2010, Textron (Year: 2010).*
Janice Taylor, The Total Guide to Carrier Oils: 21 of the Best To Mix With Essential Oils, Sep. 27, 2016, Natural Living Ideas (Year: 2016).*
Written Opinion of the International Searching Authority in PCT/US2019/045739 (dated Nov. 21, 2019).
International Search Report in PCT/US2019/045739 (dated Nov. 21, 2019).
The Olive Oil Source "Omega-3 and Omega-6 Fatty Acids." The Olive Oil Source, 2013, www.oliveoilsource.com/definition/omega-3-and-omega-6-fatty-acids.
Prescription Skin Care. "Retinol H10 in Exfol A Plus." Prescription Skin Care, Apr. 11, 2017, www.prescriptionskincare.co.nz/blog/retinol-h10-exfol-plus/.

* cited by examiner

*Primary Examiner* — Abigail Vanhorn
*Assistant Examiner* — Ali S Saeed
(74) *Attorney, Agent, or Firm* — Pryor Cashman LLP

(57) ABSTRACT

A cosmetic concentrate base composition and cosmetic compositions for use as creams or lotions utilizing the same, the cosmetic concentrate base composition including approximately 20% to 25% by weight of a first component, the first component being a phospholipid component; approximately 10% to 40% by weight of a second component, the second component being a lipid component; and approximately 4% to 5% by weight of a third component, the third component being a hydrophilic component.

10 Claims, 15 Drawing Sheets

Traditional Cosmetic Compositions

Human Natural Skin Matrix

Cosmetic Composition #1

Human Natural Skin Matrix

Average TEWL Measurement
At Baseline to Week 4

Average Corneometer Measurement (Face) At Baseline to Week 4

Average Chromameter Measurement
At Baseline to Week 4 (Pigmentation at one spot)

COSMETIC BASE COMPOSITIONS AND ASSOCIATED COSMETIC COMPOSITIONS

CROSS-REFERENCE TO RELATED APPLICATIONS

The present application claims priority to U.S. Provisional Patent Application No. 62/715,951, filed Aug. 8, 2018, the disclosures and teachings of which are incorporated herein by reference.

TECHNICAL FIELD

The present invention generally relates to cosmetic compositions. More particularly, the present invention relates to a cosmetic concentrate base as well as creams, lotions, and the like utilizing the cosmetic concentrate base.

BACKGROUND OF THE INVENTION

In the field of cosmetic compositions, creams and lotions typically include chemical emulsifiers to stabilize the oils and water contained therein. These emulsifiers, however, may act to disrupt and/or wash away the natural protective barriers of the user's skin, thereby inhibiting the ability of the user's skin to function properly. Therefore, there is a need for a cosmetic composition that functions to mimic the user's skin and consequently preserve the natural protective barriers of the user's skin while also providing a greater vehicle for delivery of active ingredients to and within the user's skin.

SUMMARY OF THE INVENTION

In general, in one aspect, the invention features a cosmetic concentrate base composition including approximately 20% to 25% by weight of a first component, the first component being a phospholipid component; approximately 10% to 40% by weight of a second component, the second component being a lipid component; and approximately 4% to 5% by weight of a third component, the third component being a hydrophilic component.

Implementations of the invention may include one or more of the following features. The composition may include approximately 25% by weight of the first component. The phospholipid component may include hydrogenated phosphatidylcholine. The composition may include approximately 25% by weight of the second component. The lipid component may include one or more of a medium-chain triglyceride, a phytosterol, and ceramide 3. The lipid component may include one or more of a fat or an oil that is, or is derived from, avocado, sunflower, macadamia, musk rose, and shea butter. The composition may include approximately 5% by weight of the third component. The hydrophilic component may include pentylene glycol. The composition may further include one or more of a fatty acid, a vitamin, a mineral, transretinoic acid, a tannin, and a flavonoid. The fatty acid may be Omega-3, Omega-6, Omega-7, Omega-9, and combinations thereof, and the vitamin may be Vitamin A, Vitamin B1, Vitamin B2, Vitamin C, Vitamin D, Vitamin E, and combinations thereof. The balance of the composition may be water.

In general, in another aspect, the invention features a cosmetic composition for use as a cream or a lotion, the composition including a cosmetic concentrate base composition in an amount of approximately 1% to 15% by weight.

Implementations of the invention may include one or more of the following features. The cosmetic composition may include approximately 1% by weight of the cosmetic concentrate base composition. The cosmetic composition may include approximately 12% to 15% by weight of the cosmetic concentrate base composition. The cosmetic composition may further include approximately 5% to 7% by weight of an alcohol component. The alcohol component may include one or more of glycerin/glycerol, cetearyl alcohol, and cetyl alcohol. The cosmetic composition may further include one or more additional components, each of the one or more additional components being in an amount of approximately 3% by weight or less, the one or more additional components including one or more of an acrylic acid polymer, a hydrocarbon, a fat, an oil, a medium-chain triglyceride, an oligopeptide, a vitamin, a preservative, an extract, and sodium hydroxide. The cosmetic composition may further include approximately 25% by weight of a sun protection component. The sun protection component may include one or more of titanium dioxide and zinc oxide. The cosmetic composition may further include one or more additional components, each of the one or more additional components being in an amount of approximately 4% by weight or less, the one or more additional components including an alcohol, a hydrocarbon, a surfactant, an emulsifier, a vitamin, a preservative, a powder, a film former, a thickener, an extract, and a stem cell blend.

DETAILED DESCRIPTION OF THE INVENTION

This invention provides a cosmetic concentrate base that mimics a user's skin and enhances the natural protective barriers therein. Additionally, the cosmetic concentrate base contains no chemical emulsifiers. Such a composition may be 1000 times more effective than traditional creams and lotions in terms of skin protection and/or 10 times more effective than traditional creams and lotions in terms of active ingredient delivery.

Figure 1:
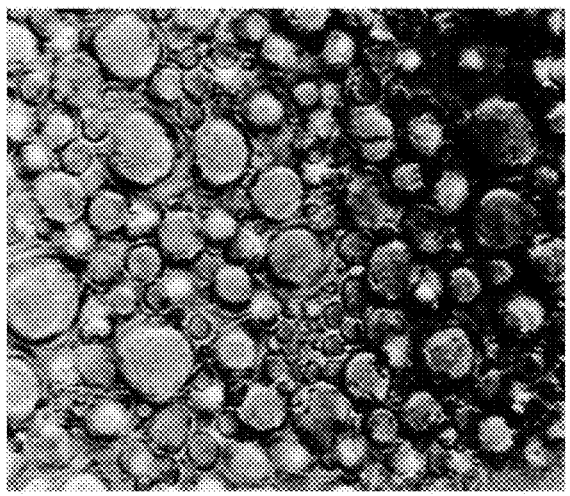
FIG. 1 illustrates a comparison between traditional cosmetic compositions utilizing chemical emulsifiers and the natural skin matrix of humans.
Figure 1:
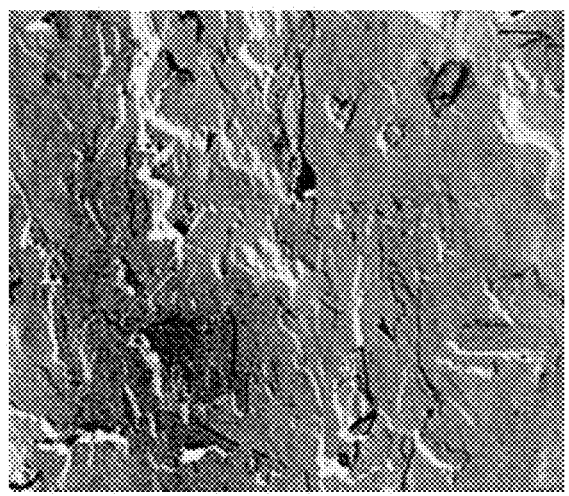

FIG. 1 shows microscopic views of traditional cosmetic compositions utilizing chemical emulsifiers and the natural skin matrix of humans. As can be seen in FIG. 1, traditional cosmetic compositions containing oil, water, and chemical emulsifiers have a droplet structure, which is distinct from, and does not support, the lamellar membrane structure of the human skin matrix. These chemical emulsifiers may destroy or wash away portions of the lamellar membrane structure of the human skin matrix.

Figure 2:
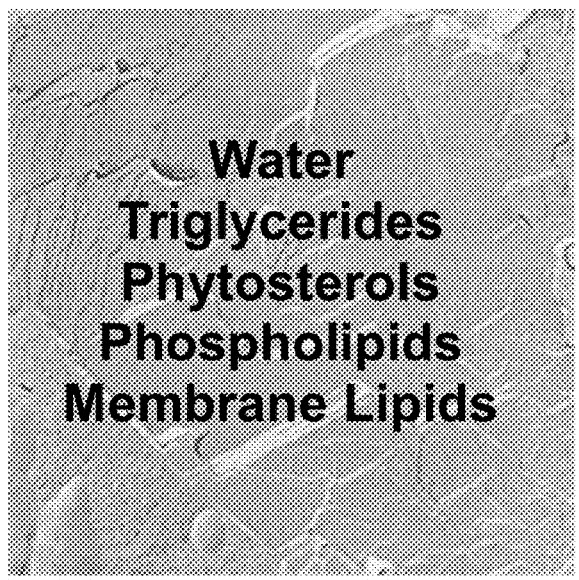
FIG. 2 illustrates a comparison between a cosmetic composition of the present invention and the natural skin matrix of humans.
Figure 2:
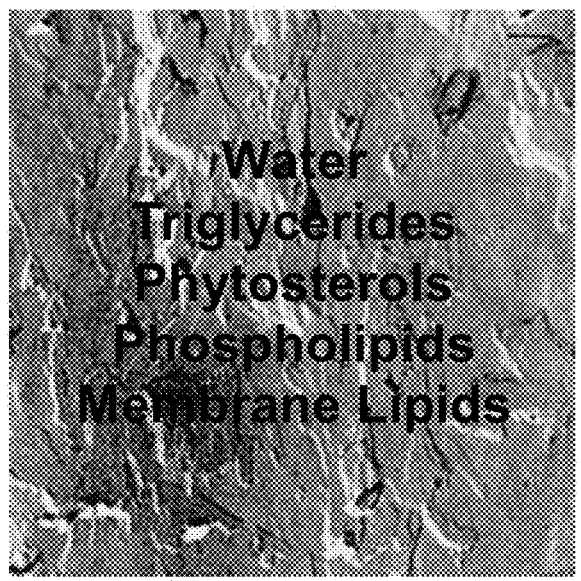

FIG. 2 shows microscopic views of a cosmetic composition of the present invention and the natural skin matrix of humans. As can be seen in FIG. 2, the structure of this cosmetic composition has a greater similarity to the lamellar membrane structure of the human skin matrix than the droplet structure of traditional cosmetic compositions. Many elements found in this cosmetic composition are also found in the human skin matrix, including water, triglycerides, phytosterols, phospholipids, and membrane lipids.

In one embodiment of the cosmetic concentrate base of the present invention, the composition includes a phospholipid component. The phospholipid component may be approximately 20%-25% of the cosmetic concentrate base composition. In one embodiment, the phospholipid component is approximately 25% of the cosmetic concentrate base composition. The phospholipid component may include one or more of any industry-acceptable phospholipid including, but not limited to, hydrogenated phosphatidylcholine.

The cosmetic concentrate base composition may also include an additional lipid component. The additional lipid component may be approximately 10%-40% of the cosmetic concentrate base composition. In one embodiment, the additional lipid component is approximately 25% of the cosmetic concentrate base composition. The additional lipid component may include one or more of any industry-acceptable lipid including, but not limited to, medium-chain triglycerides (e.g., caprylic/capric triglyceride), phytosterols, ceramide 3, and fats/oils (e.g., vegetable fats/oils, seed oils, herb oils, and plant-based oils generally). In one embodiment of the present invention, the cosmetic concentrate base composition has an additional lipid component including fats/oils that are, or derived from, avocado, sunflower, macadamia, musk rose, and shea butter.

The cosmetic concentrate base composition may also include a hydrophilic component. The hydrophilic component may be approximately 4%-5% of the cosmetic concentrate base composition. In one embodiment, the hydrophilic component is approximately 5% of the cosmetic concentrate base composition. The hydrophilic component may include one or more of any industry-acceptable hydrophilic component including, but not limited to, pentylene glycol.

The cosmetic concentrate base composition may also include water in a balancing amount. The pH of such the cosmetic concentrate base composition may be in the range of 6-7.

Benefits of this cosmetic concentrate base are manifold, with the following aspects being a subset of these benefits. First, the structure of the cosmetic concentrate base mimics the user's skin, thereby providing greater protection against foreign materials, toxins, and free radicals from penetrating the skin. Additionally, this structure provides a superior barrier for controlling transepidermal water loss. Second and relatedly, this mimicking structure assists or permits active ingredients to be more readily absorbed into the user's skin, thereby allowing these active ingredients to apply and/or develop their effects over a longer duration. Third, skin elasticity and hydration is improved as a result of higher water retention. Fourth, premature aging is lessened, as the skin is better able to maintain optimal barrier function, decreasing losses of collagen and elastin.

In one embodiment of the present invention, the cosmetic concentrate base composition includes one or more of fatty acids such as Omega-3, -6, -7, and -9, vitamins such as vitamins A, B1, B2, C, D, and E, minerals or a source thereof, transretinoic acid, tannins, and flavonoids. Through selection of such components, the cosmetic concentrate base composition has numerous benefits, including those relating to barrier function restoration, wound healing, moisturization, and antioxidant activity.

The cosmetic concentrate base composition of the present invention may be utilized as a base in a variety of cosmetic creams and lotions. In embodiments of creams and lotions not intended for use in sun protection, the cosmetic concentrate base composition may be approximately 12%-15% of the total cream or lotion composition. In embodiments of creams and lotions intended for use in sun protection, the cosmetic concentrate base composition may be used in a lower quantity, such as a quantity of approximately 1% of the total cream or lotion composition.

In embodiments of creams and lotions not intended for use in sun protection utilizing the cosmetic concentrate base composition of the present invention, an alcohol component may be included. The alcohol component may be approximately 5%-7% of the total cream or lotion composition. The alcohol component may include one or more of any industry-acceptable alcohols including, but not limited to, glycerin/glycerol, cetearyl alcohol, and cetyl alcohol. These creams and lotions may include additional components in amounts of approximately 3% or less individually of the total cream or lotion composition, and these additional components include, but are not limited to, one or more of acrylic acid polymers, hydrocarbons, fats/oils, medium-chain triglycerides, oligopeptides, vitamins, preservatives, extracts, and sodium hydroxide. These creams and lotions may also include water in a balancing amount. Water may be, e.g., approximately 65%-70% of the total cream or lotion composition.

In embodiments of creams and lotions intended for use in sun protection utilizing the cosmetic concentrate base composition of the present invention, a sun protection component may be included. The sun protection component may be approximately 25% of the total cream or lotion composition. The sun protection component may include one or more of any industry-acceptable sun protection component including, but not limited to, titanium dioxide and zinc oxide. These creams and lotions may include additional components in amounts of approximately 4% or less individually of the total cream or lotion composition, and these additional components include, but are not limited to, one or more of alcohols, hydrocarbons, surfactants (e.g., silicone surfactants and/or emulsifiers), vitamins, preservatives, powders, film formers, thickeners, extracts, and stem cell blends. These creams and lotions may also include water in a balancing amount. Water may be, e.g., approximately 25%-30% of the total cream or lotion composition.

The cosmetic concentrate base of the present invention, and the creams and lotions described herein utilizing the cosmetic concentrate base, may be produced through standard industry-acceptable processes having steps involving mixing, heating, and/or cooling the various components, intermediate mixtures, and/or final mixtures. In one embodiment of the process for producing the cosmetic concentrate base of the present invention, selected fats that are solid at room temperature should be melted before addition. The mixture relating to the cosmetic concentrate base should not exceed a temperature of approximately 60° C. Additionally, selected hydrophilic active ingredients including, but not limited to, extracts and vitamins may be pre-dissolved in water.

In one embodiment of the process for producing creams and lotions of the present invention, it is preferable that the water- and oil-phase components not be heated separately but rather mixed and homogenized simultaneously with the cosmetic concentrate base. Also, temperature-sensitive ingredients and perfume oils may be added simultaneously, while active ingredients may be incorporated into the lamellar layer structure without temperature load. Homogenization may be performed by common mixing systems including, but not limited to, dissolvers, rotor-stator stirrers, and stirring rods. Use of relatively high shear forces is possible without destroying the membrane structure.

Experimental Example 1

In a first experimental example concerning a cosmetic concentrate base composition of the present invention, the composition underwent Fourier transform infrared (FTIR) spectroscopy to evaluate skin penetration characteristics.

Figure 3:
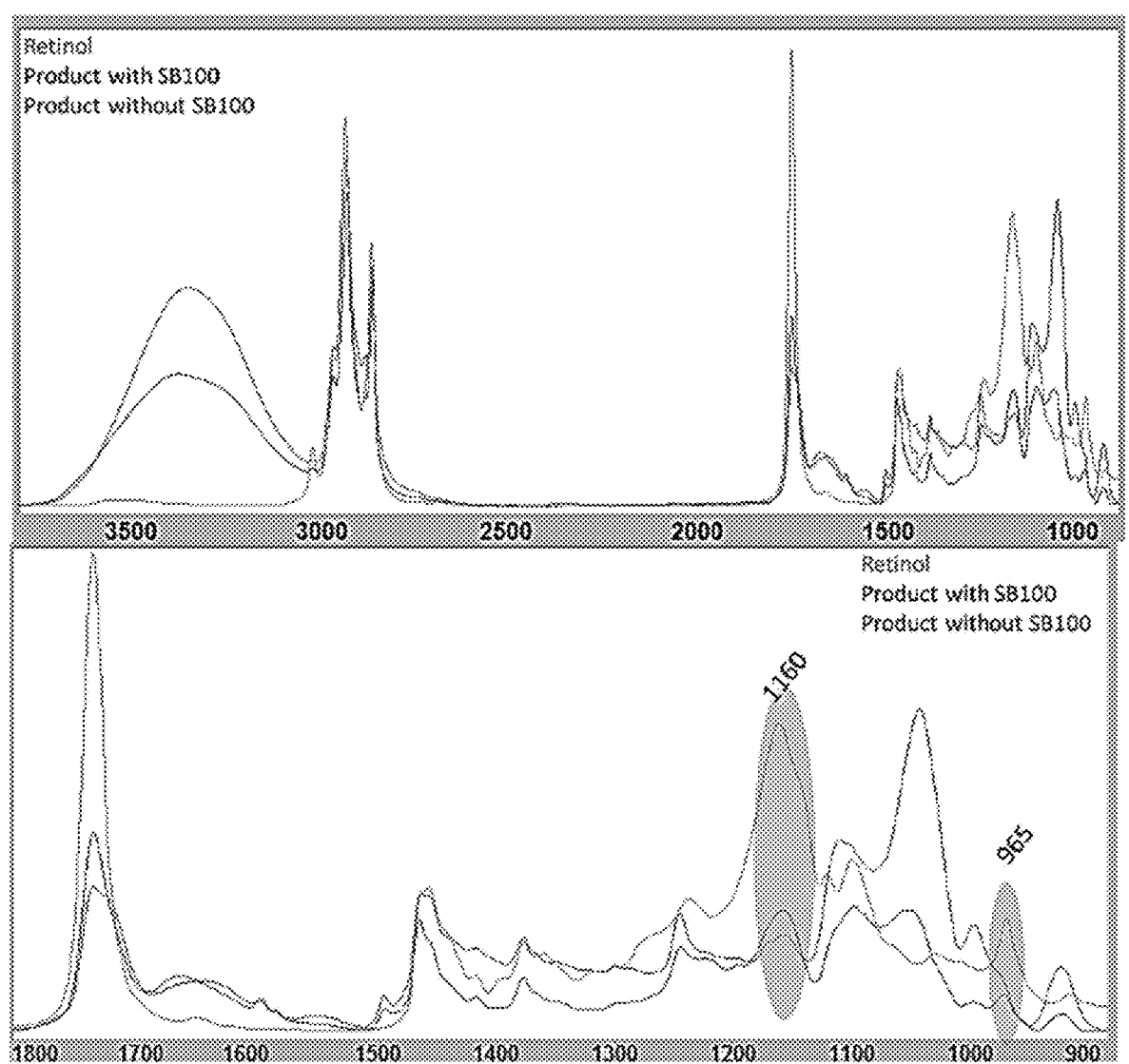
FIG. 3 illustrates FTIR spectra results for Retinol, a 4.5% Retinol formulation with a cosmetic composition of the present invention, and a 4.5% Retinol formulation without a cosmetic composition of the present invention.
Figure 4:
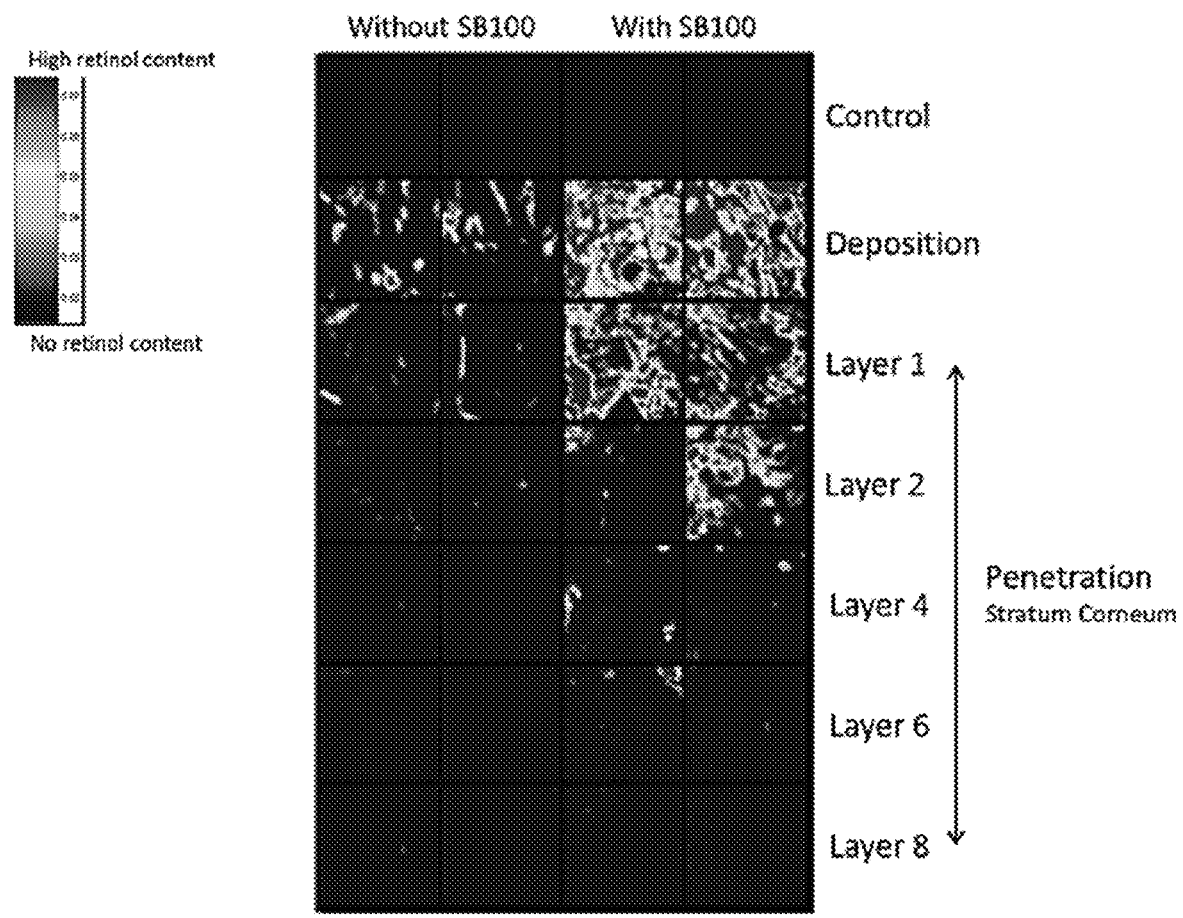
FIG. 4 illustrates ATR-FTIR data of Retinol distribution in human skin samples treated with and without a cosmetic composition of the present invention.

An ex vivo study was performed utilizing two samples: (1) human skin treated with a 4.5% Retinol formulation without the composition, and (2) human skin treated with a 4.5% Retinol formulation with the composition. Attenuated total reflection (ATR)-FTIR images were collected at the surface of the human skin samples. The two formulations were applied in excess topically on respective human skin samples and placed in a Franz cell setup for 2 hours at 32° C. After 2 hours, the formulations were removed from the human skin samples. Additional ATR-FTIR images were collected. In order to investigate the retinol penetration inside the stratum corneum, eight (8) tape strips were applied and removed from the skin surfaces. Different depths inside the stratum corneum were obtained through this tape stripping method. This method permitted imaging of the surface of the stratum corneum as well as five (5) layers under the surface (i.e., after tape strip 1, 2, 4, 6, and 8). ATR-FTIR imaging was performed on a Spotlight 400 device (PerkinElmer) (Spectral Resolution 4 $cm^{-1}$; Spatial Resolution 6.25 µm; Scan Accumulation 4; Spectral Range 4000-750 $cm^{-1}$). FIG. 3 shows FTIR spectra results for Retinol (in red), the 4.5% Retinol formulation with the composition (in black), and the 4.5% Retinol formulation without the composition (in blue). FIG. 4 shows an ATR-FTIR image in the 965 $cm^{-1}$ band area to visualize Retinol distribution in the human skin samples, in which a redder color is indicative of higher Retinol content and a bluer color is indicative of lower Retinol content. It was determined that the deposition of retinol at the skin surface was significantly higher in skin samples treated with the formulation containing the composition, that the highest penetration of Retinol was observed in the sample treated with the formulation containing the composition, and that the Retinol penetrated deeper into the stratum corneum when formulated with the composition.

Experimental Example 2

In a second experimental example concerning a cosmetic concentrate base composition of the present invention, a four-week in vivo clinical study was performed for a niacinamide gel serum containing the composition.

Figure 5:
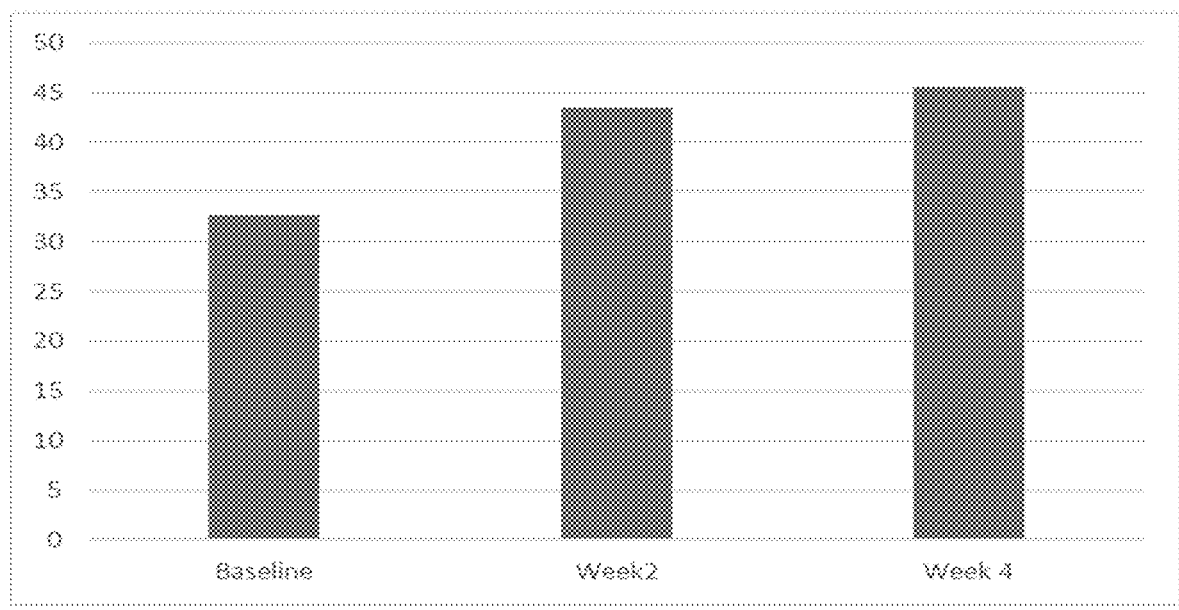
FIG. 5 illustrates average corneometer measurements on facial skin of subjects in a four-week study concerning a niacinamide gel serum containing a cosmetic composition of the present invention.
Figure 6:
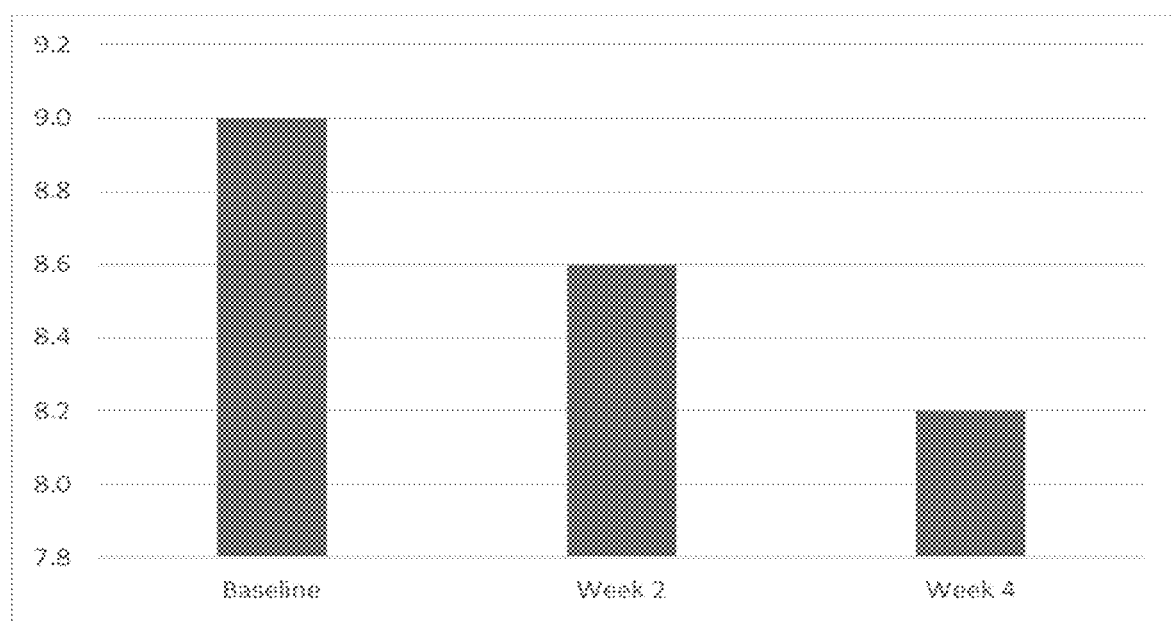
FIG. 6 illustrates average transepidermal water loss (TEWL) measurements on skin of subjects in a four-week study concerning a niacinamide gel serum containing a cosmetic composition of the present invention.

A total of 34 subjects were enrolled in the study, with 30 subjects having completed week 4. As shown in FIG. 5, average corneometer measurements on facial skin of the subjects increased after the four-week study, indicating improved skin moisture content and improved skin hydration. As shown in FIG. 6, average transepidermal water loss (TEWL) measurements decreased after the four-week study, indicating a reduction in water loss and improvement in water retention in the skin. These positive results demonstrate improved skin barrier function leading to improved skin hydration after four weeks of product application. Based on skin instrument measurements performed after four weeks of product application, it was determined that improvements ranged from 6% to 50%, with positive results including improvement in skin brightness.

Experimental Example 3

In a third experimental example concerning a cosmetic concentrate base composition of the present invention, an eight-week in vivo clinical study was performed for a niacinamide gel serum containing the composition.

Figure 7:
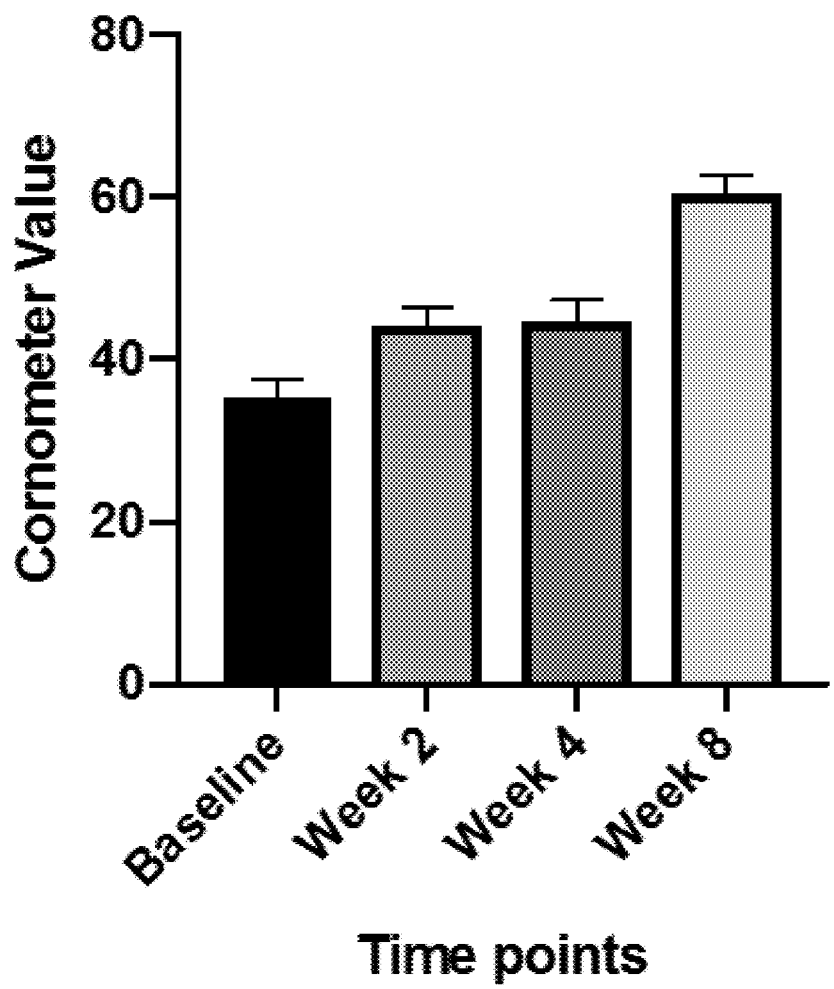
FIG. 7 illustrates average corneometer measurements on facial skin of subjects in an eight-week study concerning a niacinamide gel serum containing a cosmetic composition of the present invention.
Figure 8:
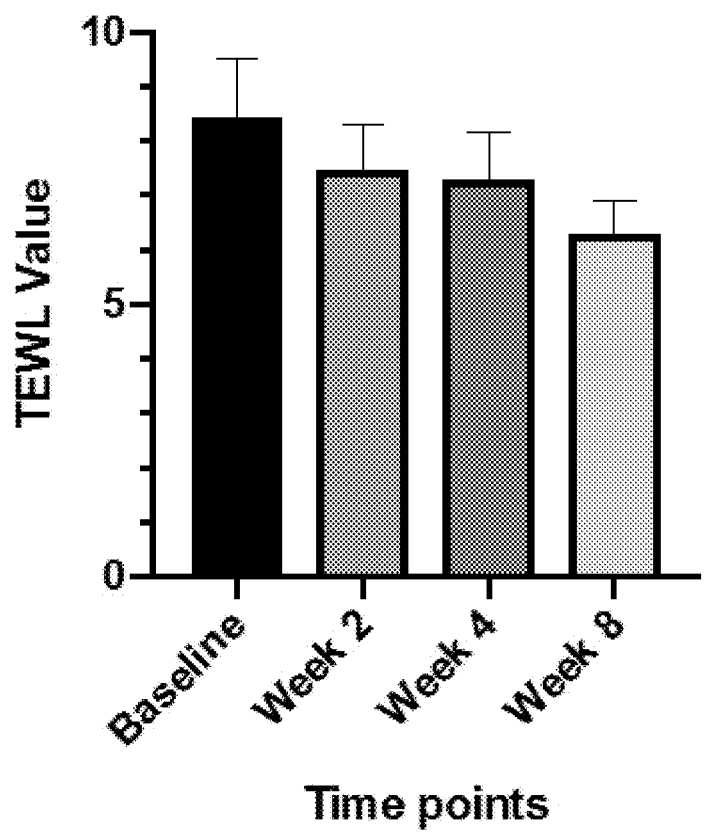
FIG. 8 illustrates average TEWL measurements on skin of subjects in an eight-week study concerning a niacinamide gel serum containing a cosmetic composition of the present invention.

A total of 34 subjects were enrolled in the study. As shown in FIG. 7, average corneometer measurements on facial skin of the subjects increased after the eight-week study, specifically 22.1% at week 2, 23.6% at week 4, and 67.0% at week 8, indicating improved skin moisture content and improved skin hydration. As shown in FIG. 8, average TEWL measurements decreased after the eight-week study, specifically 13.6% at week 2, 17.2% at week 4, and 21.9% at week 8, indicating a reduction in water loss and improvement in water retention in the skin. These positive results demonstrate improved skin barrier function leading to improved skin hydration after eight weeks of product application. Based on skin instrument measurements performed after eight weeks of product application, improvements were detected regarding various aspects, with no adverse events reported.

Experimental Example 4

In a fourth experimental example concerning a cosmetic concentrate base composition of the present invention, a four-week in vivo clinical study was performed for a Retinol night treatment containing the composition.

Figure 9:
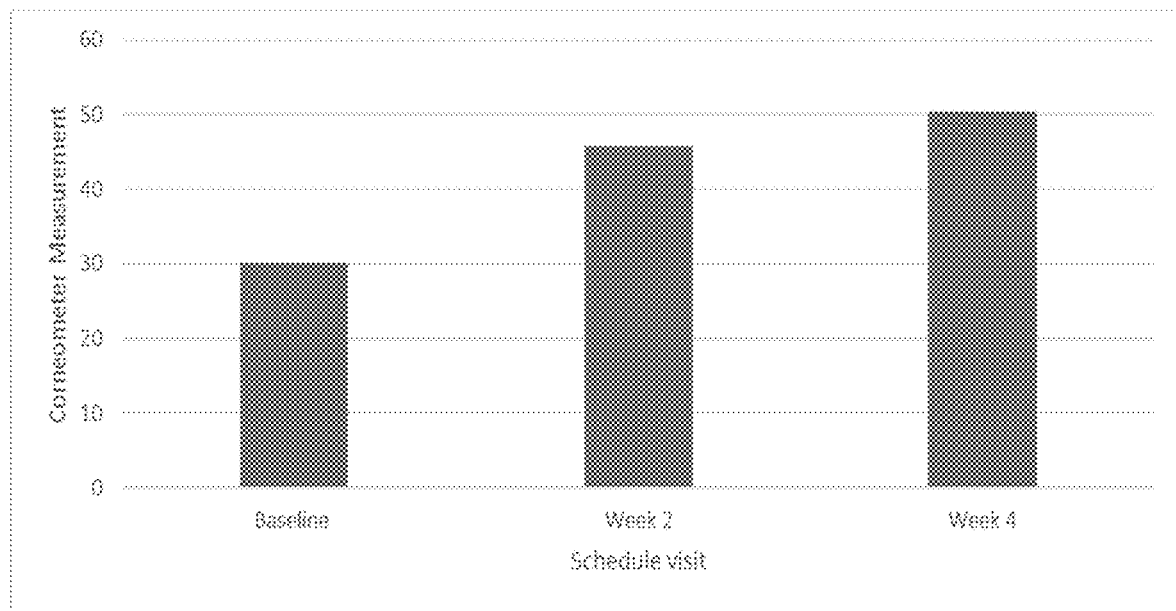
FIG. 9 illustrates average corneometer measurements on facial skin of subjects in a four-week study concerning a Retinol night treatment containing a cosmetic composition of the present invention.
Figure 10:
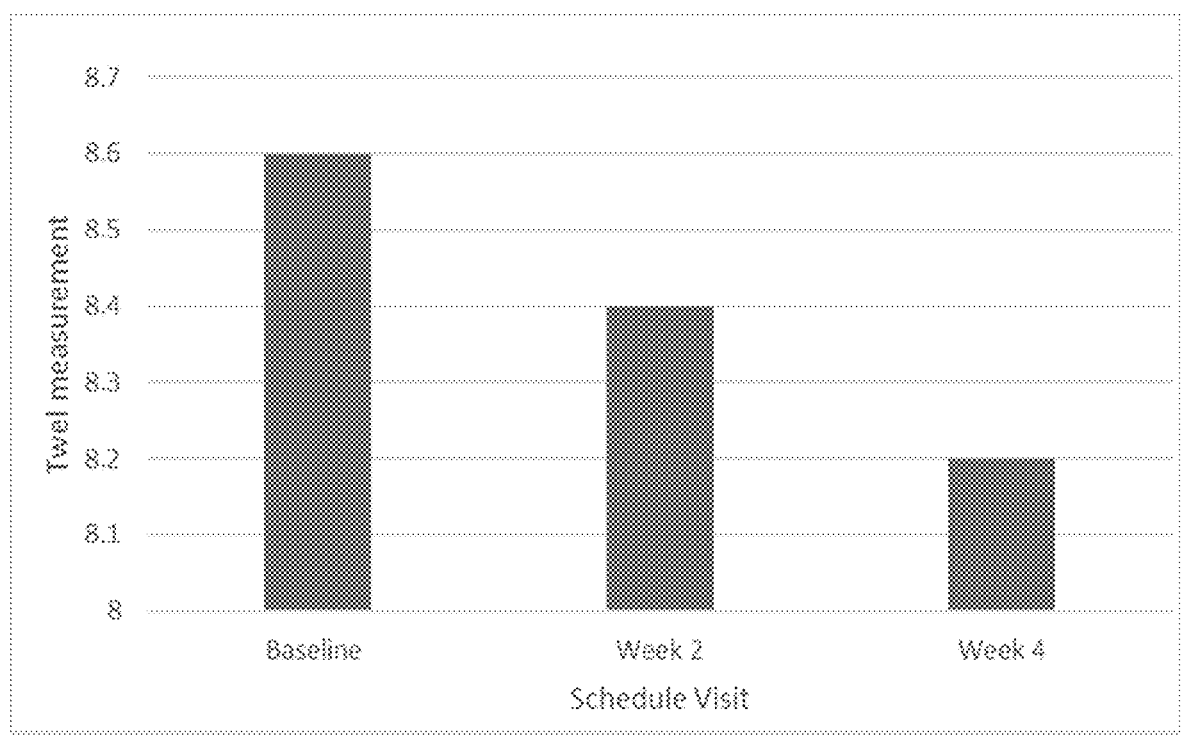
FIG. 10 illustrates average transepidermal water loss (TEWL) measurements on skin of subjects in a four-week study concerning a Retinol night treatment containing a cosmetic composition of the present invention.

A total of 32 subjects were enrolled in the study, with 28 subjects having completed week 4. As shown in FIG. 9, average corneometer measurements on facial skin of the subjects increased after the four-week study, indicating improved skin moisture content and improved skin hydration. As shown in FIG. 10, average TEWL measurements decreased after the four-week study, indicating a reduction in water loss and improvement in water retention in the skin. These positive results demonstrate improved skin barrier function leading to improved skin hydration after four weeks of product application. Based on skin instrument measurements performed after four weeks of product application, it was determined that improvements ranged from 6% to 50%, with no adverse events reported.

Experimental Example 5

In a fifth experimental example concerning a cosmetic concentrate base composition of the present invention, an eight-week in vivo clinical study was performed for a Retinol night treatment containing the composition.

Figure 11:
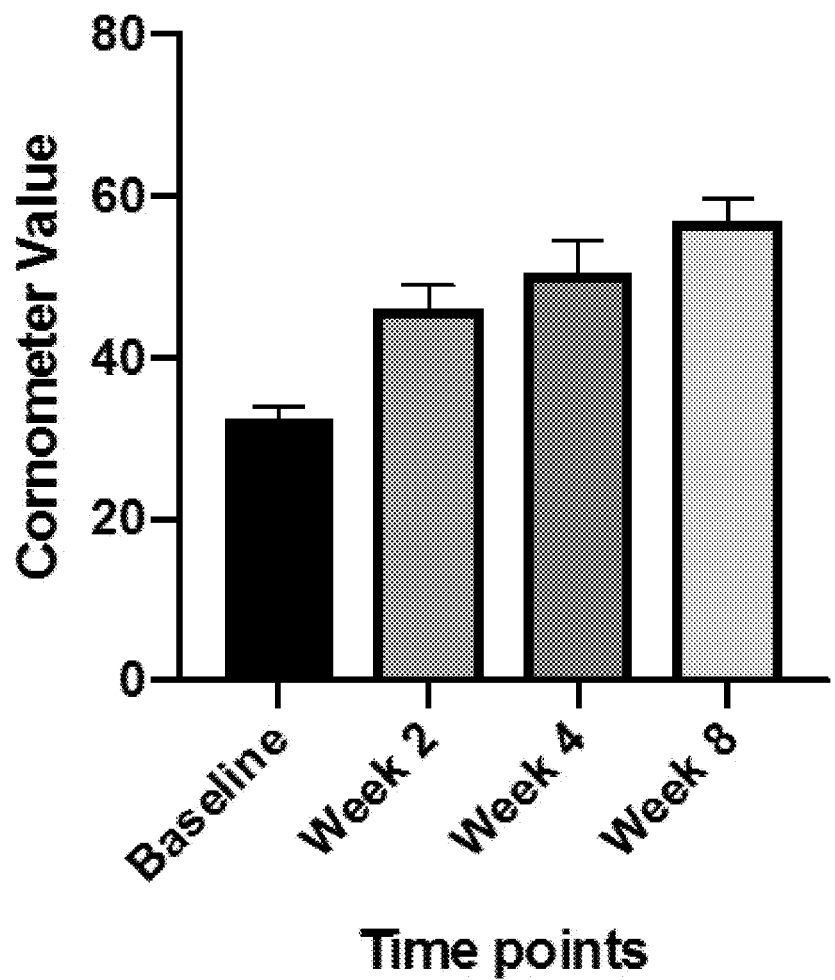
FIG. 11 illustrates average corneometer measurements on facial skin of subjects in an eight-week study concerning a Retinol night treatment containing a cosmetic composition of the present invention.
Figure 12:
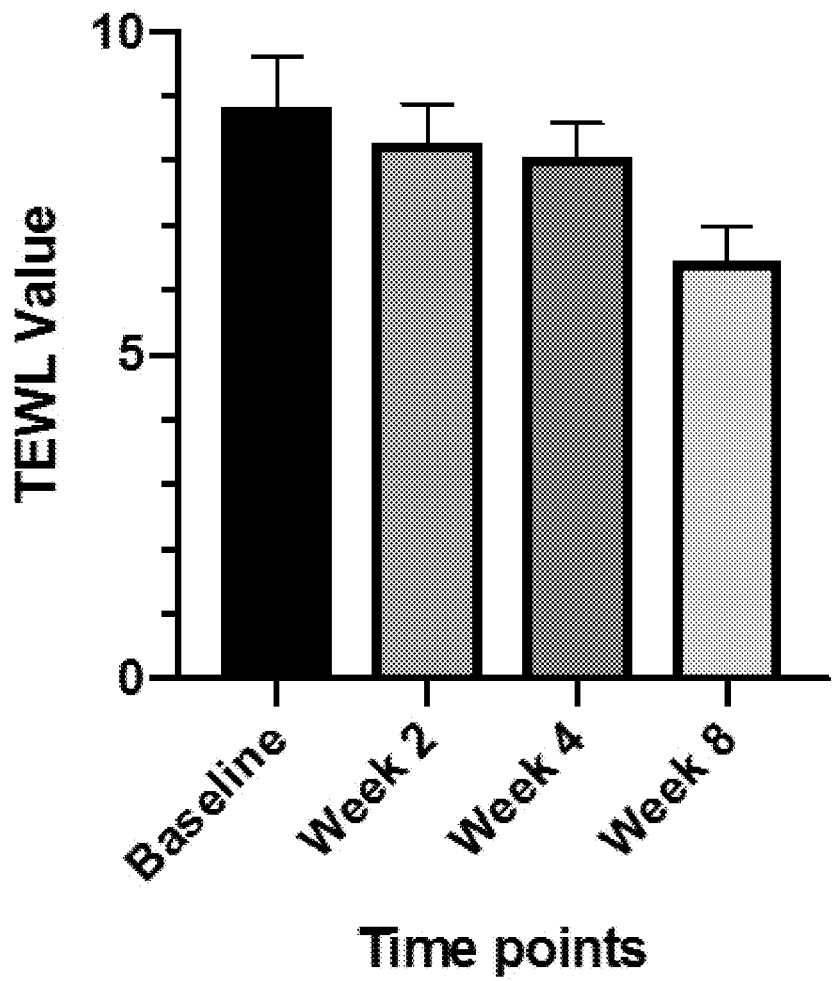
FIG. 12 illustrates average TEWL measurements on skin of subjects in an eight-week study concerning a Retinol night treatment containing a cosmetic composition of the present invention.

A total of 33 subjects were enrolled in the study. As shown in FIG. 11, average corneometer measurements on facial skin of the subjects increased after the eight-week study, specifically 27.1% at week 2, 39.5% at week 4, and 57.9% at week 8, indicating improved skin moisture content and improved skin hydration. As shown in FIG. 12, average TEWL measurements decreased after the eight-week study, specifically 6.33% at week 2, 9.03% at week 4, and 23.7% at week 8, indicating a reduction in water loss and improvement in water retention in the skin. These positive results demonstrate improved skin barrier function leading to improved skin hydration after eight weeks of product application. Based on skin instrument measurements performed after eight weeks of product application, improvements were detected regarding various aspects, with no adverse events reported.

Experimental Example 6

In a sixth experimental example concerning a cosmetic concentrate base composition of the present invention, a four-week in vivo clinical study was performed for a Vitamin C serum containing the composition.

Figure 13:
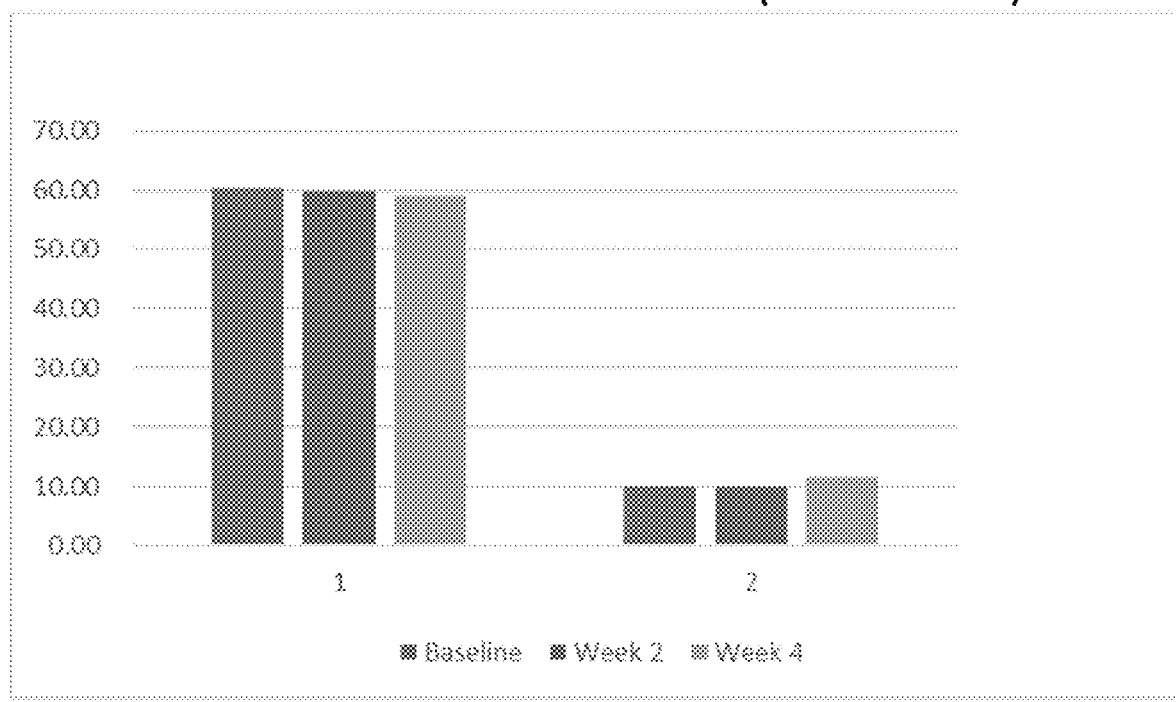
FIG. 13 illustrates average chromameter measurements on skin tone of subjects in a four-week study concerning a Vitamin C serum containing a cosmetic composition of the present invention.
Figure 14:
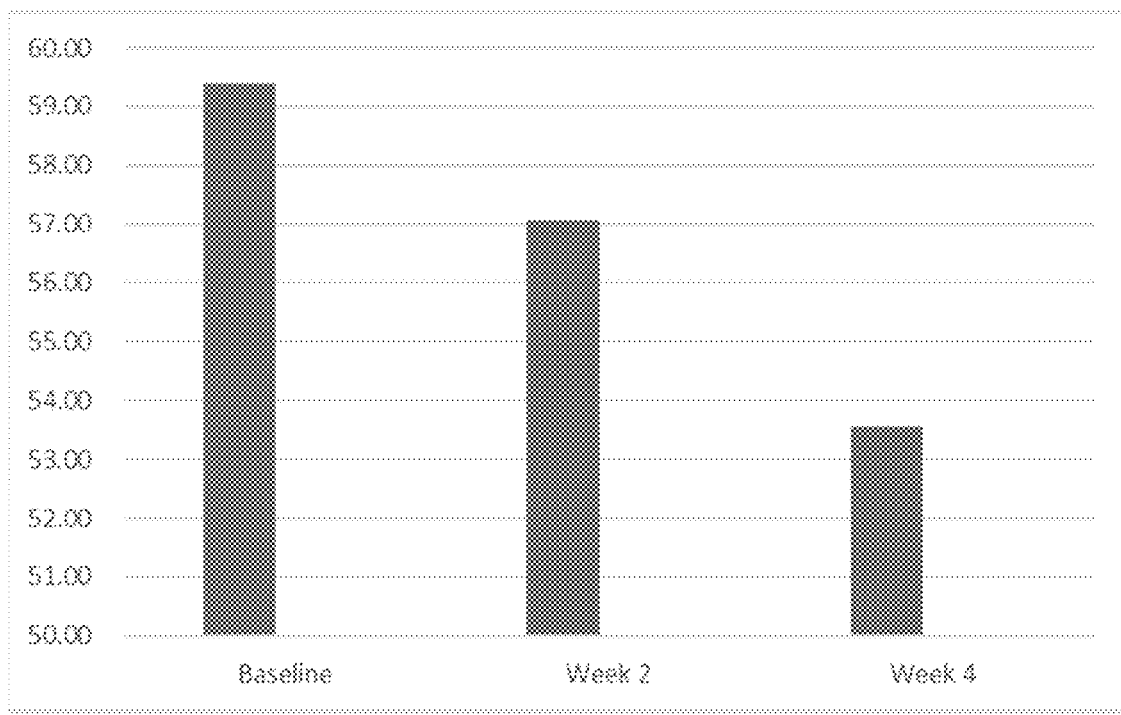
FIG. 14 illustrates average chromameter measurements on pigmentation at one facial skin location on subjects in a four-week study concerning a Vitamin C serum containing a cosmetic composition of the present invention.

A total of 32 subjects were enrolled in the study, with 26 subjects having completed week 4. As shown in FIG. 13, average chromameter measurements on skin tone of the subjects indicated a reduction in dark spots and improvement in skin brightness after the four-week study. As shown in FIG. 14, average chromameter measurements on pigmentation at one facial skin location on the subjects indicated a decrease in pigmentation after the four-week study. Based on skin instrument measurements performed after four weeks of product application, improvements in skin homogeneity and reductions in dark spots were detected, with no adverse events reported.

Experimental Example 7

In a seventh experimental example concerning a cosmetic concentrate base composition of the present invention, an eight-week in vivo clinical study was performed for a Vitamin C serum containing the composition.

Figure 15:
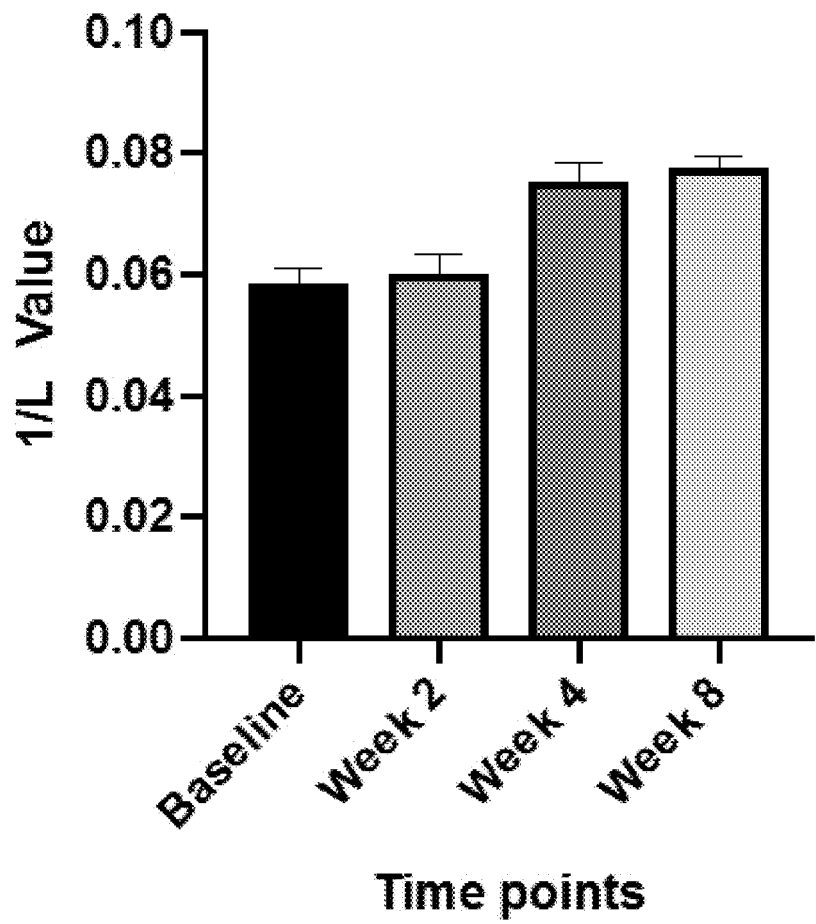
FIG. 15 illustrates average chromameter measurements on facial skin of subjects in an eight-week study concerning a Vitamin C serum containing a cosmetic composition of the present invention.

A total of 30 subjects were enrolled in the study. As shown in FIG. 15, average chromameter measurements on facial skin of the subjects increased after the eight-week study, specifically 2.87% at week 2, 28.7% at week 4, and 33.0% at week 8, indicating an improvement in skin brightness. Based on skin instrument measurements performed after eight weeks of product application, improvements were detected regarding various aspects, with no adverse events reported.

The embodiments and examples above are illustrative, and many variations can be introduced to them without departing from the spirit and scope of the disclosure or from the scope of the invention. For example, elements and/or features of different illustrative and exemplary embodiments herein may be combined with each other and/or substituted with each other within the scope of this disclosure. For a better understanding of the invention, its operating advantages and the specific objects attained by its uses, reference should be had to the drawings and descriptive matter, in which there is illustrated a preferred embodiment of the invention.

What is claimed is:

1. A cosmetic concentrate base composition consisting of:
   (a) approximately 20% to 25% by weight of a first component, the first component being a phospholipid component;
   (b) approximately 25% by weight of a second component, the second component being a lipid component comprising a medium-chain triglyceride, a phytosterol, ceramide 3, avocado oil, sunflower oil, macadamia oil, musk rose oil, and shea butter;
   (c) approximately 4% to 5% by weight of a third component, the third component being a hydrophilic component;
   (d) optionally one or more of a fatty acid, a vitamin, a mineral, transretinoic acid, a tannin, or a flavonoid; and
   (e) a balance in water.

2. The cosmetic concentrate base composition of claim 1, wherein the composition comprises approximately 25% by weight of the first component.

3. The cosmetic concentrate base composition of claim 1, wherein the phospholipid component comprises hydrogenated phosphatidylcholine.

4. The cosmetic concentrate base composition of claim 3, wherein the composition comprises approximately 5% by weight of the third component.

5. The cosmetic concentrate base composition of claim 3, wherein the hydrophilic component comprises pentylene glycol.

6. The cosmetic concentrate base composition of claim 1, wherein the fatty acid is Omega-3, Omega-6, Omega-7, Omega-9, and combinations thereof.

7. The cosmetic concentrate base composition of claim 1, wherein the vitamin is Vitamin A, Vitamin B1, Vitamin B2, Vitamin C, Vitamin D, Vitamin E, and combinations thereof.

8. A cosmetic concentrate base composition consisting of:
   (a) approximately 20% to 25% by weight of a first component, the first component being a phospholipid component;
   (b) approximately 10% to 40% by weight of a second component, the second component being a lipid component comprising a medium-chain triglyceride, a phytosterol, ceramide 3, avocado oil, sunflower oil, macadamia oil, musk rose oil, and shea butter;

(c) approximately 4% to 5% by weight of a third component, the third component being a hydrophilic component;

(d) optionally one or more of a fatty acid, a vitamin, a mineral, transretinoic acid, a tannin, or a flavonoid, wherein the fatty acid is Omega-3, Omega-6, Omega-7, Omega-9, and combinations thereof, and wherein the vitamin is Vitamin A, Vitamin B1, Vitamin B2, Vitamin C, Vitamin D, Vitamin E, and combinations thereof; and (e) a balance in water.

9. The cosmetic concentrate base composition of claim 8, wherein the phospholipid component comprises hydrogenated phosphatidylcholine.

10. The cosmetic concentrate base composition of claim 8, wherein the hydrophilic component comprises pentylene glycol.

* * * * *